United States Patent
Lushka

(10) Patent No.: US 12,343,413 B2
(45) Date of Patent: Jul. 1, 2025

(54) VEGAN SEMI-SOLID COSMETIC COMPOSITION

(71) Applicant: L'ORÉAL, Paris (FR)

(72) Inventor: Monika Lushka, Towaco, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/864,646

(22) Filed: Jul. 14, 2022

(65) Prior Publication Data

US 2024/0016713 A1    Jan. 18, 2024

(51) Int. Cl.
| | |
|---|---|
| *A61Q 19/00* | (2006.01) |
| *A61K 8/19* | (2006.01) |
| *A61K 8/25* | (2006.01) |
| *A61K 8/58* | (2006.01) |
| *A61K 8/92* | (2006.01) |
| *A61Q 1/02* | (2006.01) |

(52) U.S. Cl.
CPC .............. *A61K 8/19* (2013.01); *A61K 8/25* (2013.01); *A61K 8/585* (2013.01); *A61Q 1/02* (2013.01); *A61K 2800/30* (2013.01); *A61K 2800/33* (2013.01); *A61K 2800/43* (2013.01); *A61K 2800/87* (2013.01)

(58) Field of Classification Search
CPC .. A61K 2800/31; A61K 8/25; A61K 2800/43; A61K 2800/48; A61K 8/31; A61K 2800/10; A61K 8/92; A61K 9/0014; A61K 8/891; A61K 8/585; A61K 8/922; A61Q 1/02; A61Q 19/00; A61Q 1/00; A61Q 19/00
See application file for complete search history.

(56) References Cited

U.S. PATENT DOCUMENTS

| | | | |
|---|---|---|---|
| 6,991,782 B2 | 1/2006 | Kanji et al. | |
| 9,649,264 B2 | 5/2017 | Ferrari et al. | |
| 10,626,294 B2 | 4/2020 | Pistorio et al. | |
| 2007/0166271 A1 | 7/2007 | Gordon et al. | |
| 2008/0305067 A1* | 12/2008 | Bui | A61Q 1/02 424/78.37 |
| 2009/0214458 A1* | 8/2009 | Brun | A61Q 5/12 424/70.6 |
| 2011/0002869 A1 | 1/2011 | Barba et al. | |
| 2011/0038820 A1 | 2/2011 | Barba et al. | |
| 2012/0328539 A1* | 12/2012 | Tamura | C08G 77/14 424/59 |
| 2013/0171078 A1* | 7/2013 | Lawson | A61Q 17/04 424/59 |
| 2017/0360682 A1* | 12/2017 | Debeaud | A61K 8/31 |

FOREIGN PATENT DOCUMENTS

| | | |
|---|---|---|
| FR | 2930142 A1 | 10/2009 |
| KR | 20190080447 A | 7/2019 |
| WO | 20080155059 A2 | 12/2008 |
| WO | 2009130090 A1 | 10/2009 |
| WO | 2016097119 A1 | 6/2016 |

OTHER PUBLICATIONS

French Search Report, and Written Opinion, for corresponding French Application No. 2210898, dated Oct. 21, 2022.

* cited by examiner

*Primary Examiner* — Tracy Liu
(74) *Attorney, Agent, or Firm* — MEAGHER EMANUEL LAKS GOLDBERG & LIAO, LLP

(57) ABSTRACT

A vegan anhydrous semi-solid composition may be provided, that includes at least 30% by weight of an organic solvent, a rheology modifier system, 5-15% by weight of waxes, and a particulate. The rheology modify system includes disteardimonium hectorite and silica silylate, where there is a ratio R1 of a percent by weight of disteardimonium hectorite to silica silylate that is 2.1≤R1≤6. The waxes include a hard wax and a soft wax. The particulate includes a pigment, a pearlescent agent, a filler, or a combination thereof.

18 Claims, No Drawings

VEGAN SEMI-SOLID COSMETIC COMPOSITION

TECHNICAL FIELD

The present disclosure is drawn to cosmetic compositions, and specifically vegan, semi-solid, pigmented, stable cosmetic compositions.

BACKGROUND

To satisfy modern customers, cosmetic compositions, including, e.g., mascara compositions, must meet an ever-increasing list of technical criteria, including, inter alia, being able to provide a high pigment load, have a long-lasting, aesthetic appearance and desirable texture, and be shelf stable. Achieving all the desired characteristics can be challenging, requiring substantial experimentation.

To complicate this issue, as awareness of the origins of cosmetic ingredients becomes more of a concern to customers, the number of available ingredients that can be utilized is reduced. Because of that, the ability to satisfy all customer requirements while also being, e.g., vegan, is extremely challenging.

BRIEF SUMMARY

In some embodiments, a vegan anhydrous semi-solid cosmetic composition may be provided. The composition may include at least 30% by weight of an organic solvent. The composition may include a rheology modifier system that utilizes disteardimonium hectorite and silica silylate, where a ratio R1 of a percent by weight of disteardimonium hectorite to silica silylate is $2.1 \leq R1 \leq 6$. The composition may include 5-15% by weight of waxes, the waxes comprising a hard wax and a soft wax. The composition may include a particulate consisting of a pigment, a pearlescent agent, a filler, or a combination thereof.

In some embodiments, the composition may include at least 30% by weight of the particulate. In some embodiments, the particulate may include 10-25% by weight of the composition of a filler. In some embodiments, the particulate may include 10-25% by weight of the composition of a pigment, a pearlescent agent, or a combination thereof.

In some embodiments, the composition may include 3-5% by weight of the rheology modifier system.

In some embodiments, the composition may include 30-40% by weight of the organic solvent. In some embodiments, the organic solvent may include a hydrocarbon-based oil, a glycol, and a carbonate.

In some embodiments, the composition may include 7.5-12.5% by weight of waxes. In some embodiments, the waxes may be selected such that a ratio R2 of a percent by weight of total hard waxes to total soft waxes is $1.8 \leq R2 \leq 3.5$.

In some embodiments, the composition may include a non-volatile silicone oil. In some embodiments, the composition may be free of surfactants and emulsifiers.

In some embodiments, the composition may consist of the organic solvent, the rheology modifier system, the waxes, the particulate, the non-volatile silicone oil, and a film former. In some embodiments, the film former may consist of three silicone-based film formers.

In some embodiments, a cosmetic product may be provided that includes a hand-held container (such as a tube, bottle, or jar) and a vegan anhydrous semi-solid composition as disclosed herein.

DETAILED DESCRIPTION

The present disclosure allows for production of cosmetic compositions that are, e.g., vegan, long-wear, highly pigmented semi-solid anhydrous hot pour formulation with a cream or mousse-like texture that delivers matte and pearly shades for multi-use application (e.g., eye, lip, and face).

As is understood in the art, texture is an important, subjective characteristic of a composition, and As used herein, the term "substantially free" means that there is less than 1% by weight of a specific material added to a composition, based on the total weight of the composition. Nonetheless, the compositions may include less than about 0.75 wt. %, less than about 0.5 wt. %, less than about 0.25 wt. %, less than about 0.1 wt. %, or none of the specified material.

As used herein, the term "stable" means that the composition does not exhibit phase separation and/or crystallization for a period of time, for example, for at least 1 day (24 hours), one week, one month, or one year.

As used herein, the term "volatile" means having a flash point of less than 100° C.

As used herein, the term "non-volatile" means having a flash point of 100° C. or greater.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All ranges and values disclosed herein are inclusive and combinable. For examples, any value or point described herein that falls within a range described herein can serve as a minimum or maximum value to derive a sub-range, etc.

In some embodiments, a vegan anhydrous semi-solid cosmetic composition may be provided. The composition may include an organic solvent, a rheology modifier system, waxes, and a particulate. In some embodiments, the composition may be free of surfactants and emulsifiers.

Organic Solvent

The composition may include at least 30% by weight of an organic solvent. In some embodiments, the composition may include 30-40% by weight of the organic solvent. In some embodiments, the composition may comprise or consist of a hydrocarbon-based oil, a polyol, and a carbonate. In some embodiments, the composition may comprise or consist of a hydrocarbon-based oil, a glycol, and a carbonate. In some embodiments, the composition may comprise or consist of a hydrocarbon-based oil, and may be substantially free of both a glycol and a carbonate.

Hydrocarbon-Based Oil

In some embodiments, the organic solvent may include a hydrocarbon-based oil. The hydrocarbon-based oil is an oil that is liquid at room temperature (25° C.).

The term "hydrocarbon-based oil" means an oil formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

In some embodiments, the hydrocarbon-based oil may be volatile or non-volatile. In some embodiments, the hydrocarbon-based oil may be chosen from hydrocarbon-based oils containing from 8 to 14 carbon atoms, and especially:
(1) branched $C_8$-$C_{14}$ alkanes, for instance $C_8$-$C_{14}$ isoalkanes of petroleum origin (also known as isoparaffins), for instance isododecane (also known as 2,2,4,4,6- pentamethylheptane), isodecane and, for example, the oils sold under the trade name Isopar or Permethyl;

(2) linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof, (3) short-chain esters (containing from 3 to 8 carbon atoms in total) such as ethyl acetate, methyl acetate, propyl acetate or n-butyl acetate;

(4) hydrocarbon-based oils of plant origin such as triglycerides constituted of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel;

(5) synthetic ethers having from 10 to 40 carbon atoms;

(6) linear or branched hydrocarbons of mineral or synthetic origin, such as petroleum jelly, polydecenes, hydrogenated polyisobutene such as Parleam®, squalane and liquid paraffins, and mixtures thereof, (7) synthetic esters such as oils of formula $R_1COOR_2$ in which $R_1$ represents a linear or branched fatty acid residue containing from 1 to 40 carbon atoms and $R_2$ represents an, in particular branched, hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters; and (8) fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

In some embodiments, the hydrocarbon-based oil may be chosen from hydrocarbon-based oils containing from 8 to 14 carbon atoms, in particular the apolar oils described previously. Preferentially, the hydrocarbon-based oil is a branched $C_8$-$C_{14}$ alkane, and more preferably, the hydrocarbon-based oil is isododecane.

In some embodiments, the hydrocarbon-based oil may be present in an amount of 30-40% by weight of the composition. In some embodiments, the hydrocarbon-based oil may be present in an amount of 35-40% by weight of the composition.

Polyol

In some embodiments, the organic solvent may include a polyol. The polyol may be a liquid polyol at ambient temperature, $C_2$-$C_8$, preferably $C_3$-$C_6$, saturated or not, linear or branched, comprising from 2 to 6 hydroxyl groups. In some embodiments, the organic solvent may include a glycol, such as a $C_3$-$C_8$ glycol. The $C_3$-$C_8$ glycol may be linear or branched, and may be saturated or unsaturated. Non-limiting examples of glycols include propylene glycol, butylene glycol, pentylene glycol, caprylyl glycol, dipropylene glycol, as well as mixtures thereof. In some embodiments, the glycol is caprylyl glycol.

In some embodiments, the glycol may be present in an amount of 0.5-5% by weight of the composition. In some embodiments, the glycol may be present in an amount of 0.5-2% by weight of the composition. In some embodiments, the composition may be substantially free of the glycol.

Carbonate

In some embodiments, the organic solvent may include a carbonate. In some embodiments, the carbonate may be an alkyl or alkylene carbonate.

In some embodiments, the alkylene chain(s) of the alkylene carbonate(s) and/or the alkyl radical(s) of the alkyl carbonate(s) may include from 1 to 6 carbon atoms, preferably from 2 to 6 carbon atoms, and more preferably from 2 to 4 carbon atoms, and may be substituted by one or more hydroxyl groups.

In some embodiments, the sum of the carbons of the alkylene chain(s) of alkylene carbonate(s) and/or the sum of the carbons of the alkyl group(s) of the alkyl carbonate(s) present in the composition range from 2 to 6 carbon atoms.

In some embodiments, the alkylene carbonate may have a structure according to formula (1):

(1)

where R' denotes a hydrogen atom, a linear or branched $C_1$-$C_6$ alkyl radical, a linear or branched $C_1$-$C_4$ hydroxyalkyl radical; R" represents a hydrogen atom, a linear or branched $C_1$-$C_6$ alkyl radical, a linear or branched $C_1$-$C_4$ hydroxyalkyl radical; and m is 1, 2 or 3.

Preferably, the radical R' represents a hydrogen atom, a linear or branched $C_1$-$C_4$ alkyl radical, a linear or branched $C_1$-$C_2$ hydroxyalkyl radical; R" represents a hydrogen atom, a linear or branched $C_1$-$C_2$ alkyl radical, a linear or branched $C_1$-$C_2$ hydroxyalkyl radical; and m=1

In some embodiments, the radical R' represents a hydrogen atom (corresponding to ethylene carbonate), a methyl group (corresponding to propylene carbonate), ethyl (corresponding to 1,2-butylene carbonate), hydroxymethyl (R'=—$CH_2OH$; corresponding to glyceryl carbonate).

In some embodiments, the carbonate is an alkylene carbonate. In some embodiments, the alkalene carbonate is propylene carbonate.

In some embodiments, the alkyl carbonate may have a structure according to formula (2):

$$R'\text{—}O\text{—}CO\text{—}O\text{—}R'' \qquad (2)$$

where R' denotes a linear or branched $C_1$-$C_5$ alkyl radical, a linear or branched $C_1$-$C_4$ hydroxyalkyl radical; R" represents a linear or branched $C_1$-$C_5$ alkyl radical, a linear or branched $C_1$-$C_4$ hydroxyalkyl radical; and the sum of the carbons of R' and R" ranging from 2 to 6.

Preferably, the radical R' represents a linear $C_1$-$C_3$ alkyl radical, a linear $C_1$-$C_2$ hydroxyalkyl radical; and R" represents a linear $C_1$-$C_3$ alkyl radical, a linear $C_1$-$C_2$ hydroxyalkyl radical.

In some embodiments, the carbonate may be an alkyl carbonate. In some embodiments, the alkyl carbonate may be diethyl carbonate and/or dipropyl carbonate.

In some embodiments, the carbonate may be present in an amount of 0.5-5% by weight of the composition. In some embodiments, the carbonate may be present in an amount of 0.9-2% by weight of the composition. In some embodiments, the composition may be substantially free of the carbonate.

Rheology Modifier System

The composition may include a rheology modifier system that comprises or consists of disteardimonium hectorite and silica silylate. The disteardimonium hectorite and silica silylate may be present in sufficient amounts such that a ratio R1 of a percent by weight of disteardimonium hectorite to a percent by weight of silica silylate is $2.1 \leq R1 \leq 6$. That is, if the formula comprises 1.0% by weight of silica silylate, the disteardimonium hectorite is present in an amount of 2.1-6% by weight of the composition. In some embodiments, the ratio R1 is $2.1 \leq R1 \leq 4$. In some embodiments, the ratio R1 is $2.1 \leq R1 \leq 3$.

In some embodiments, the composition may include 3-5% by weight of the rheology modifier system. In some embodiments, the composition may include 3.5-4.5% by weight of the rheology modifier system.

In some embodiments, the composition comprises 3-4% by weight of the hectorite, and 1-1.5% by weight of the silica silylate. In some embodiments, the composition comprises 1.4% by weight of the silica silylate.

In some embodiments, the composition is free, or substantially free, of any other rheology modifiers.

Waxes

The composition may include 5-15% by weight of waxes, the waxes comprising a hard wax and a soft wax. In some embodiments, the waxes may include a plurality of hard waxes. In some embodiments, the waxes may include one hard wax. In some embodiments, the waxes may include a plurality of soft waxes. In some embodiments, the waxes may include one soft wax.

As used herein, "wax" is intended to mean a lipophilic fatty compound that is solid at room temperature (about 25° C.) and atmospheric pressure (760 mm Hg, i.e., 105 Pa), which undergoes a reversible solid/liquid change of state and which has a melting point of greater than 30° C., and in some embodiments, greater than about 55° C. up to about 120° C., or even as high as about 200° C.

As used herein, the term "soft wax" refers to waxes which have a melting point of below about 60° C. As used herein, the term "hard wax" refers to waxes other than soft waxes—that is, waxes which have a melting point of equal to or greater than about 60° C.

Non-limiting examples of soft waxes may include paraffin wax and ceresin wax.

Non-limiting examples of hard waxes may include carnauba wax, microcrystalline wax, synthetic wax, candelilla wax, beeswax, synthetic beeswax, and ozokerite.

In some embodiments, the composition may include 7.5-12.5% by weight of waxes. In some embodiments, the waxes may be selected such that a ratio R2 of a percent by weight of total hard waxes to a percent by weight of total soft waxes is $1.8 \leq R2 \leq 3.5$.

In some embodiments, the composition may include 4.5-7% by weight of hard waxes. In some embodiments, the composition may include 2-3% by weight of soft waxes.

Particulate

In some embodiments, the composition may include a particulate consisting of a pigment, a pearlescent agent, a filler, or a combination thereof. In some embodiments, the composition may include particulates in an amount of at least 30% by weight of the composition. In some embodiments, the composition may include particulates in an amount of 30-40% by weight of the composition. In some embodiments, the composition may include particulates in an amount of 30-35% by weight of the composition. In some embodiments, the particulate may include 10-25% by weight of the composition of a pigment, a pearlescent agent, or a combination thereof.

Pigment

In some embodiments, the particular may include a pigment. As used herein, the term "pigment" refers generally to inorganic or organic, white or colored particles. Said pigments may optionally be surface-treated within the scope of the present invention but are not limited to treatments such as silicones, perfluorinated compounds, lecithin, and amino acids.

Examples of suitable pigments include, but are not limited to, inorganic pigments, organic pigments, lakes, iridescent or optically variable pigments, and mixtures thereof.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570) and mixtures thereof.

In some embodiments, a plurality of pigments are present.

In some embodiments, the composition may include 0.1-25% by weight of a pigment. In some embodiments, the composition may include 1-20% by weight of a pigment. In some embodiments, the composition may include 5-20% by weight of a pigment. In some embodiments, the composition may be substantially free of a pigment. In some embodiments, the composition may be free of a pigment.

Pearlescent Agent

In some embodiments, the particulate may include a pearlescent agent. As used herein, the term "pearlescent agents" refers to colored particles of any shape, which are or are not iridescent, in particular produced by certain molluscs in their shells or else synthesized, and which exhibit a color effect via optical interference. Such pearlescent agents are distinct from the pigments described herein.

The pearlescent agents may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles, at the surface of which are superposed at least two successive layers of metal oxides and/or of organic colorants.

Examples of nacres that may also be mentioned include natural mica covered with titanium oxide, with iron oxide, with natural pigment or with bismuth oxychloride. Among the nacres available on the market, mention may be made of the nacres Timica, Flamenco and Duochrome (based on mica) sold by the company Engelhard, the Timiron nacres sold by the company Merck, the Prestige mica-based nacres sold by the company Eckart, and the Sunshine synthetic mica-based nacres sold by the company Sun Chemical.

The nacres may more particularly have a yellow, pink, red, bronze, orangey, brown, gold and/or coppery color or glint.

Mention may in particular be made, by way of illustration of pearlescent agents which can be used in the context of the present invention, of pearlescent agents of gold color sold in particular by Engelhard under the names Brilliant Gold 212G (Timica), Gold 222C (Cloisonne), Sparkle Gold (Timica), Gold 4504 (Chromalite) and Monarch Gold 233X (Cloisonne); bronze pearlescent agents sold in particular by Merck under the names Bronze Fine (17384) (Colorona) and Bronze (17353) (Colorona) and by Engelhard under the name Super Bronze (Cloisonne); orange pearlescent agents sold in particular by Engelhard under the names Orange 363C (Cloisonne) and Orange MCR 101 (Cosmica) and by Merck under the names Passion Orange (Colorona) and Matte Orange (17449) (Microna); brown-coloured pearlescent agents sold in particular by Engelhard under the names Nu-Antique Copper 340XB (Cloisonne) and Brown CL4509 (Chromalite); pearlescent agents with a copper glint sold in particular by Engelhard under the name Copper 340A (Timica); pearlescent agents with a red glint sold in particular by Merck under the name Sienna Fine (17386) (Colorona); pearlescent agents with a yellow glint sold in particular by Engelhard under the name Yellow (4502) (Chromalite); red-colored pearlescent agents with a gold glint sold in particular by Engelhard under the name Sunstone G012 (Gemtone); pink pearlescent agents sold in particular by Engelhard under the name Tan Opale G005 (Gemtone); black pearlescent agents with a gold glint sold in particular by Engelhard under the name Nu-Antique Bronze 240 AB (Timica); blue pearlescent agents sold in particular by Merck under the name Matte Blue (17433) (Microna); white pearlescent agents with a silvery glint sold in particular by Merck under the name Xirona Silver; and golden green pinkish orangey pearlescent agents sold in particular by Merck under the name Indian Summer (Xirona), and mixtures thereof.

In some embodiments, the pearlescent agent is mica.

In some embodiments, the composition may include 0.1-10% by weight of a pearlescent agent. In some embodiments, the composition may include 1-9% by weight of a pearlescent agent. In some embodiments, the composition may include 2-8% by weight of a pearlescent agent. In some embodiments, the composition may include 3-7% by weight of a pearlescent agent. In some embodiments, the composition may include 4-6% by weight of a pearlescent agent. In some embodiments, the composition may be substantially free of a pearlescent agent. In some embodiments, the composition may be free of a pearlescent agent.

Filler

In some embodiments, the particulate may include a filler. As used herein, the term "filler" refers to a particle of organic or inorganic nature which is colourless or white, which is solid, which has any shape and which is insoluble in the medium of the composition at ambient temperature and atmospheric pressure. These fillers are advantageously dispersed in the composition. As used herein, the term "inorganic" refers to any compound, the chemical structure of which does not comprise a carbon atom. Such fillers are distinct from the pigments and pearlescent agents described herein.

In some embodiments, the fillers may not be surface-coated. In some embodiments, the fillers may be surface-coated, and in particular they can be surface-treated with silicones, amino acids, fluorinated derivatives or any other substance which promotes the dispersion and compatibility of the filler in the composition.

In some embodiments, the fillers may be spherical, that is to say comprise at least a rounded general portion, preferably defining at least a sphere portion, preferably internally defining a concavity or a hollow (sphere, globules, bowls, horseshoe, and the like), or lamellar.

Non-limiting examples of fillers include:
(1) silica powders, such as the porous silica microspheres sold under the name Silica Beads SB-700 by Miyoshi or Sunsphere® H-51 or Sunsphere® H-33 by Asahi Glass; or the polydimethylsiloxane-coated amorphous silica microspheres sold under the name SA Sunsphere® H-33 or SA Sunsphere® H-53 by Asahi Glass;
(2) powders of acrylic (co)polymers and their derivatives, in particular: the polymethyl methacrylate powder sold under the names Covabead® LH85 by Wackherr or Microsphere M-100® by Matsumoto, the polymethyl methacrylate/ethylene glycol dimethacrylate powder sold under the name Dow Corning 5640 Microsponge® Skin Oil Adsorber by Dow Corning or Ganzpearl® GMP-0820 by Ganz Chemical, the polyallyl methacrylate/ethylene glycol dimethacrylate powder sold under the name Poly-Pore® L200 or Poly-Pore® E200 by Amcol Health and Beauty Solutions Inc., the ethylene glycol dimethacrylate/lauryl methacrylate copolymer powder sold under the name Polytrap® 6603 by Dow Corning, the optionally crosslinked acrylate/alkyl acrylate copolymer such as crosslinked acrylate/ethylhexyl acrylate copolymer powder sold under the name Techpolymer ACP-8C by Sekisui Plastics, ethylene/acrylate copolymer powder, such as that sold under the name Flobeads® by Sumitomo Seika Chemicals, the expanded hollow particles of acrylonitrile (co)polymer sold under the name Expancel by Expancel or the microspheres sold under the name Micropearl F 80 ED® by Matsumoto, (3) polyurethane powders, for example sold under the names Plastic Powder D-400, Plastic Powder CS-400, Plastic Powder D-800 and Plastic Powder T-75 by Toshiki, (4) silicone powders advantageously chosen from:
- polymethylsilsesquioxane powders, in particular those sold under the name Tospearl, in particular Tospearl 145 A, by Momentive Performance Materials,
- organopolysiloxane elastomer powders coated with silicone resin, in particular with silsesquioxane resin, such as the products sold under the name KSP-100, KSP-101, KSP-102, KSP-103, KSP-104 or KSP-105 by Shin-Etsu (INCI name: vinyl dimethicone/methicone silsesquioxane crosspolymer),
- powders of silicone elastomers, such as the products sold under the name Trefil® Powder E-505C or Trefil® Powder E-506C by Dow Corning,
- powders of organosilicone particles, for example, in the form of bowls, such as those described in JP-2003 128 788 or JP-A-2000-191789 or also in Application EP 1 579 841 and sold in particular by Takemoto Oil & Fat, (5) polyamide powders, such as Nylon® powders, in particular Nylon 12 powders, such as the nylon powders sold under the name Orgasol® 2002 EXS NAT COS by Arkema, (6) powders of natural organic materials, such as polysaccharide powders and in particular starch powders, especially crosslinked or non-crosslinked maize, wheat or rice starch powders, powders of starch crosslinked by octenylsuccinic anhydride sold under the name Dry-Flo® by National Starch or powders of waxy maize starch, such as those which are sold under the names C* Gel 04201 by Cargill, Maize Starch B by Roquette and Organic Corn Starch by Draco Natural Products, (7) spherical cellulose microparticles, such as Cellulobeads D-10, Cellulobeads D-5 and Cellulobeads USF, sold by Daito Kasei Kogyo, (8) particles of N—(C8-C22 acylated) amino acids; the amino acid can, for example, be lysine, glutamic acid or alanine, preferably lysine, for example Amihope LL from Ajinomoto or also that which is sold under the name Comm 5105 S by Corum, (9) Perlite powders, such as those sold by World Minerals under the trade name Perlite P1430, Perlite P2550, Perlite P2040 or OpTiMat™ 1430 OR 2550 OR, Europerl EMP-2 and Europerl 1 by Imerys,

(10) zeolites, such as the products sold by Zeochem under the names Zeoflair 300, Zeoflair 200, Zeoflair 100, X-Mol and X-Mol MT, and

(11) calcium magnesium carbonate particles, such as those sold by Imerys under the name Calcidol, by LCW (Sensient) under the name Carbomat or by Omya under the name Omyacare S60-AV.

In some embodiments, use may also be made of talc particles, for example sold under the names Luzenac Pharma M and UM by Imerys and Rose Talc and Talc SG-2000 by Nippon Talc.

In some embodiments, use may also be made of natural or synthetic mica particles, such as those sold under the names Mica M RP and Silk Mica by Merck or also that sold under the name Sericite S-152-BC by Miyoshi Kasei; calcium carbonate and magnesium hydrogencarbonate; hydroxyapatite; boron nitride; fluorphlogopite; and their mixtures.

In some embodiments, the spherical fillers may be coated with a hydrophobic treatment agent. The hydrophobic treatment agent can be chosen from fatty acids, such as stearic acid; metal soaps, such as aluminium dimyristate or the aluminium salt of hydrogenated tallow glutamate; amino acids; N-acylated amino acids or their salts; lecithin; isopropyl triisostearyl titanate; and their mixtures. The N-acylated amino acids can comprise an acyl group having from 8 to 22 carbon atoms, such as, for example, a 2-ethylhexanoyl, caproyl, lauroyl, myristoyl, palmitoyl, stearoyl or cocoyl group. The salts of these compounds can be the aluminium, magnesium, calcium, zirconium, zinc, sodium or potassium salts. The amino acid can, for example, be lysine, glutamic acid or alanine. The term "alkyl" cited in the abovementioned compounds denotes in particular an alkyl group having from 1 to 30 carbon atoms and preferably having from 5 to 16 carbon atoms.

In some embodiments, the filler is synthetic fluorphlogopite.

In some embodiments, the composition may include 10-25% by weight of a filler. In some embodiments, the composition may include 10-15% by weight of a filler. In some embodiments, the composition may include 15-25% by weight of a filler. In some embodiments, the composition may be substantially free of a filler. In some embodiments, the composition may be free of a filler.

Non-Volatile Silicone Oil

In some embodiments, the composition may include a non-volatile silicone oil.

Non-limiting examples of non-volatile silicone oils include linear or cyclic non-volatile polydimethylsiloxanes (PDMSs); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates. In some embodiment, the non-volatile silicone oil is caprylyl methicone.

In some embodiments, the composition may include 0.1-10% by weight of a non-volatile silicone oil. In some embodiments, the composition may include 1-9% by weight of a non-volatile silicone oil. In some embodiments, the composition may include 2-8% by weight of a non-volatile silicone oil. In some embodiments, the composition may include 3-7% by weight of a non-volatile silicone oil. In some embodiments, the composition may include 4-6% by weight of a non-volatile silicone oil. In some embodiments, the composition may be substantially free of a non-volatile silicone oil. In some embodiments, the composition may be free of a non-volatile silicone oil.

Film Former as Used

In some embodiments, the composition may include a film former (sometimes referred to as a film forming agent"). In some embodiments, the composition may include one film former. In some embodiments, the composition may include a plurality of film formers. In some embodiments, the composition may include three silicone-based film formers.

As used herein, the term "Film former" or "film forming agent" or "film forming polymer" or "film forming resin" refers to a polymer or resin that leaves a film on the substrate to which it is applied, for example, after a solvent accompanying the film former has evaporated, absorbed into and/or dissipated on the substrate.

In some embodiments, the film forming agents may have at least one glass transition temperature ($T_g$) which is lower than normal human body temperature (98.6° F.). In some embodiments, the at least one film forming agents may have all of its glass transition temperature(s) below normal human body temperature (98.6° F.). The $T_g$ property of the at least one film forming agent may result from various ways known in the art such as, for example, the $T_g$ of the film forming agent itself, the combination of different film forming agents to achieve a $T_g$ lower than normal human body temperature, or the combination of film forming agent(s) and plasticizer(s) to achieve a Tg lower than normal human body temperature. Examples of acceptable classes of film forming agents include acrylic polymers, silicone resins, silicone acrylate copolymers, vinyl pyrrolidone (VP) containing homopolymers and copolymers, polyurethanes, polyolefins and mixtures thereof.

In some embodiments, the film forming agent(s) may be a silicone resin, a silicone acrylate copolymer, an acrylate copolymer, or a mixture thereof.

Silicone Resin

As used herein, the term "resin" means a crosslinked or non-crosslinked three-dimensional structure. Silicone resin nomenclature is known in the art as "MDTQ" nomenclature, whereby a silicone resin is described according to the various monomeric siloxane units which make up the polymer.

Each letter of "MDTQ" denotes a different type of unit. The letter M denotes the monofunctional unit $(CH_3)_3SiO_{1/2}$. This unit is considered to be monofunctional because the silicone atom only shares on oxygen when the unit is part of a polymer. The "M" unit can be represented by the following structure:

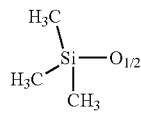

At least one of the methyl groups of the M unit may be replaced by another group, e.g., to give a unit with formula $[R(CH_3)_2]SiO_{1/2}$, as represented in the following structure:

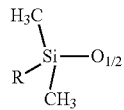

wherein R is chosen from groups other than methyl groups. Non-limiting examples of such groups other than methyl groups include alkyl groups other than methyl groups, alkene groups, alkyne groups, hydroxyl groups, thiol groups, ester groups, acid groups, ether groups, wherein the groups other than methyl groups may be further substituted.

The symbol D denotes the difunctional unit $(CH_3)_2SiO_{2/2}$ wherein two oxygen atoms bonded to the silicone atom are used for binding to the rest of the polymer. The "D" unit, which is the major building block of dimethicone oils, can be represented as:

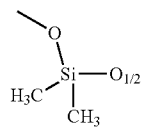

At least one of the methyl groups of the D unit may be replaced by another group, e.g., to give a unit with formula $[R(CH_3)_2]SiO_{1/2}$.

The symbol T denotes the trifunctional unit, $(CH_3)SiO_{3/2}$ and can be represented as:

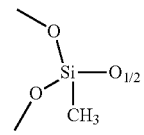

At least one of the methyl groups of the T unit may be replaced by another group, e.g., to give a unit with formula $[R(CH_3)_2]SiO_{1/2}$.

Finally, the letter Q means a tetrafunctional unit $SiO_{4/2}$ in which the silicon atom is bonded to four hydrogen atoms, which are themselves bonded to the rest of the polymer.

Thus, a vast number of different silicone polymers can be manufactured. Further, it would be clear to one skilled in the art that the properties of each of the potential silicone polymers will vary depending on the type(s) of monomer(s), the type(s) of substitution(s), the size of the polymeric chain, the degree of cross linking, and size of any side chain(s).

Non-limiting examples of silicone polymers include siloxysilicates and silsesquioxanes.

A non-limiting example of a siloxysilicate is trimethylsiloxysilicate, which may be represented by the following formula: $[(CH_3)_3XSiXO]_xX(SiO_{4/2})_y$, (i.e., MQ units) wherein x and y may, for example, range from 50 to 80. Silsesquioxanes, on the other hand, may be represented by the following formula: $(CH_3SiO_{3/2})_x$ (i.e., T Units) wherein x may, for example, have a value of up to several thousand.

Resin MQ, which is available from Wacker, General Electric and Dow Corning, is an example of an acceptable commercially-available siloxysilicate. For example, trimethylsiloxysilicate (TMS) is commercially available from General Electric under the tradename SR1000 and from Wacker under the tradename TMS 803. TMS is also commercially available from Dow Chemical in a solvent, such as for example, cyclomethicone.

Non-limiting examples of silicon resin comprising at least one T unit are disclosed, for example, in U.S. patent applications 2007/0166271, 2011/0038820, 2011/0002869, and 2009/0214458, the entire contents of which are hereby incorporated by reference in their entirety.

In embodiments where the silicone resin contains at least one T unit, it may thus be, for example, a T, MT, MTQ or MDTQ resin.

In some embodiments, the unit composition of the silicone resin can be at least 50% T units, or at least 70% T units, or at least 80% T units, or at least 90% T units.

In the M, D and T units listed as examples above, at least one of the methyl groups may be substituted. In some embodiments, at least one silicone resin comprising at least one trifunctional unit of formula $(R)SiO_{3/2}$ may be chosen from the silsesquioxanes of formula: $((R')SiO_{3/2})_x$, in which x ranges from 100 to 500 and R' is chosen, independently by trifunctional unit, from a hydrocarbon-based group containing from 1 to 10 carbon atoms or a hydroxyl group, on the condition that at least one R' is a hydrocarbon-based group. According to preferred embodiments, the hydrocarbon-based group containing from 1 to 10 carbon atoms is a methyl group. According to preferred embodiments, the at least one silicone resin comprising at least one trifunctional unit of formula $(R)SiO_{3/2}$ is chosen from the silsesquioxanes of the formula: $((R')SiO_{3/2})_x$, in which x ranges from 100 to 500 and R' is chosen, independently by unit, from $CH_3$, a hydrocarbon-based group containing from 2 to 10 carbon atoms, or a hydroxyl group, on the condition that at least one R' is a hydrocarbon-based group.

In some embodiments, the T resins may contain M, D and Q units such that at least 80 mol % or at least 90 mol %, relative to the total amount of silicones, are T units. The T resins may also contain hydroxyl and/or alkoxy groups. The T resins may have a total weight of hydroxyl functions ranging from 2% to 10% and a total weight of alkoxy functions that may be up to 20%; in some embodiments, the total weight of hydroxyl functions ranges from 4% to 8% and the total weight of alkoxy functions may be up to 10%.

In some embodiments, the silicone resin may be chosen from silsesquioxanes that are represented by the following formula: $((CH_3)SiO_{3/2})_x$, in which x may be up to several thousand and the $CH_3$ group may be replaced with an R group, as described previously in the definition of the T units. The number x of T units of the silsesquioxane may be less than or equal to 500, or it may range from 50 to 500, including all ranges and subranges therebetween. The molecular weight of the silicone resin may range from 500 to 50,000 g/mol, from 500 to 20,000 g/mol, or from 500 to 10,000 g/mol, including all ranges and subranges therebetween.

Non-limiting examples of these silicone resins containing at least one T unit include:
(1) polysilsesquioxanes of formula $((R)SiO_{3/2})_x$ (T units) in which x is greater than 100, in which the R groups may independently be methyl or other substituents as defined above;
(2) polymethylsilsesquioxanes, which are polysilsesquioxanes in which R is a methyl group. Such polymethylsilsesquioxanes are described, for example, in U.S. Pat. No. 5,246,694 the entire contents of which is hereby incorporated by reference in its entirety;
(3) polypropylsilsesquioxanes, in which R is a propyl group. These compounds and their synthesis are described, for example, in patent application WO 2005/075567, the entire contents of which is hereby incorporated by reference in its entirety; and
(4) polyphenylsilsesquioxanes, in which R is a phenyl group. These compounds and their synthesis are described, for example, in patent application US 2004/0180011, the entire contents of which is hereby incorporated by reference in its entirety.

Examples of commercially available polymethylsilsesquioxane resins that may be mentioned include those sold by the company Wacker under the reference Resin MK such as Belsil PMS MK: polymer comprising $CH_3SiO_{3/2}$ repeating units (T units), which may also comprise up to 1% by weight of $(CH_3)_2SiO_{2/2}$ units (D units) and having an average molecular weight of about 10 000 g/mol. It is thought that the polymer is in a "cage" and "ladder" configuration as represented in the figures below. The average molecular weight of the units in "cage" configuration has been calculated as 536 g/mol. The majority of the polymer is in the "ladder" configuration with ethoxy groups at the ends. These ethoxy groups represent 4.5% by mass of the polymer. As these end groups can react with water, a small and variable amount of SiOH groups may also be present; and by the company Shin-Etsu under the references KR-220L, which are composed of T units of formula $CH_3SiO_{3/2}$ and have Si—OH (silanol) end groups, under the reference KR-242A, which comprise 98% of T units and 2% of dimethyl D units and have Si—OH end groups or alternatively under the reference KR-251 comprising 88% of T units and 12% of dimethyl D units and have Si—OH end groups.

Examples of commercially available polypropylsilsesquioxane resins that may be mentioned include those sold by the company Dow Corning under the reference Dow Corning 670 Fluid or 680 Fluid. Typically such commercially available products are polypropylsilsesquioxane diluted in volatile oil such as volatile hydrocarbon oil or volatile silicone oil such as D5. Dow Corning 670 and 680 Fluids have a general formula of $R_nSiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

Examples of commercially available polyphenylsilsesquioxane resins include those sold by the company Dow Corning under the reference Dow Corning 217 Flake Resin, which is a polyphenylsilsesquioxane with silanol end groups; and by the company Wacker under the reference Belsil SPR 45 VP.

In some embodiments, the film forming agent include trimethylsiloxysilicate. In some embodiments, the film forming agent may include polypropylsilsesquioxane. In some embodiments, the film forming agent may include C30-45 alkyldimethylsilyl polypropylsilsesquioxane. In some embodiments, the film forming agent may comprise or consist of trimethylsiloxysilicate, polypropylsilsesquioxane, and C30-45 alkyldimethylsilyl polypropylsilsesquioxane.

In some embodiments, the composition may consist of the organic solvent, the rheology modifier system, the waxes, the particulate, the non-volatile silicone oil, and the film former.

Example 1

The formulations shown in Tables 1 and 2, below, may be made using an enclosed-system kettle with homogenizer capability. First, the hectorite and solvents (including the organic solvent) are homogenized to create a smooth, gel-like consistency. Next, the remaining ingredients, except for any pearlescent agents, are added and homogenized under high temperatures until a homogenous mixture is achieved. Lastly, the pearlescent agents are mixed into the batch until a uniform shade is achieved (if contained in the formula). The composition can then be hot-poured into an appropriate container, such as a hand-held container, such as a tube, bottle, or jar. Note that the formulas in Table 1, while expressing ranges, the exact values are selected so as to fall within the disclosed ranges described herein.

TABLE 1

Exemplary Formulations.

| Material | Ex. 1 | Ex. 2 | Ex. 3 | Ex. 4 |
|---|---|---|---|---|
| Isododecane | 35-40% | 35-40% | 35-40% | 35-40% |
| Propylene Carbonate | 0.8-1.2% | 0.8-1.2% | 0.8-1.2% | 0.8-1.2% |
| Caprylyl Glycol | 0.4-0.6% | 0.4-0.6% | 0.4-0.6% | 0.4-0.6% |
| Disteardimonium Hectorite | 3-4% | 3-4% | 3-4% | 2-3% |
| Silica Silylate | 1-1.5% | 1-1.5% | 1-1.5% | 1-1.5% |
| Filler | 10-12% | 20-25% | 1-10% | 20-25% |
| Pearlescent Agent | — | 5-10% | 25-30% | 5-10% |
| Pigments | 15-20% | 5-10% | 1-10% | 5-10% |
| Hard Waxes | 6.5-7.5% | 6.5-7.5% | 5.5-6.5% | 4.5-5.5% |
| Soft Waxes | 1.5-2.5% | 1.5-2.5% | 2-3% | 2-3% |
| Non-Volatile Silicone Oil | 3-5% | 3-5% | 3-5% | 3-5% |
| Trimethylsiloxysilicate | 8-9% | 8-9% | 8-9% | 8-9% |
| Polypropylsilsesquioxane | 4-5% | 4-5% | 4-5% | 4-5% |
| C30-45 alkyldimethylsilyl Polypropylsilsesquioxane | 0.1-1% | 0.1-1% | 0.1-1% | 0.1-1% |

TABLE 2

Comparative Formulations.

| Material | Co. 1 | Co. 2 |
|---|---|---|
| Isododecane | 36.1% | 38% |
| Propylene Carbonate | 0.8% | 0.3% |
| Caprylyl Glycol | 0.5% | 0.3% |
| Disteardimonium Hectorite | 2.7% | 1.1% |
| Silica Silylate | 1.3% | 1.5% |
| Filler | 27.5% | 11% |
| Pearlescent Agent | 5% | 0.1% |
| Pigments | 5.5% | 16.9% |
| Hard Waxes | 3% | 9% |
| Soft Waxes | — | 4% |
| Non-Volatile Silicone Oil | 4% | 4% |
| Trimethylsiloxysilicate | 8.5% | 8.6% |
| Polypropylsilsesquioxane | 4.5% | 4.6% |
| C30-45 alkyldimethylsilyl Polypropylsilsesquioxane | 0.6% | 0.6% |

Ex. 1-4 are stable formulations having a soft creamy, mousse-like texture. Conversely, while Co. 1 contains a desirable texture, it is unstable in the form of wax and solvent separation at elevated temperatures (e.g., 30-50° C.). Co. 2 is stable (including at the elevated temperatures), but lacks the desirable texture, and is also a non-vegan formulation (e.g., containing non-vegan waxes, etc.).

In some embodiments, a cosmetic product may be provided that includes a hand-held container (such as a tube, bottle, or jar) and a vegan anhydrous semi-solid composition as disclosed herein.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications.

As used herein, including in the claims, the term "and/or," used in connection with a list of items, means one or more of the items in the list, i.e., at least one of the items in the list, but not necessarily all the items in the list.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

What is claimed is:

1. A vegan anhydrous semi-solid composition comprising:
at least 30% by weight of an organic solvent selected from the group consisting of a hydrocarbon-based oil, a glycol, and a carbonate;
2-8% by weight of a non-volatile silicone oil;
a rheology modifier system comprising disteardimonium hectorite and silica silylate,
where a ratio R1 of a percent by weight of disteardimonium hectorite to silica silylate is $2.1 \leq R1 \leq 6$;
5-15% by weight of waxes, the waxes comprising a hard wax and a soft wax, where a ratio R2 of a percent by weight of total hard waxes to total soft waxes is $1.8 \leq R2 \leq 3.5$; and
a particulate consisting of a pigment, a pearlescent agent, a filler, or a combination thereof.

2. The vegan anhydrous semi-solid composition according to claim 1, wherein the composition comprises at least 30% by weight of the particulate.

3. The vegan anhydrous semi-solid composition according to claim 2, wherein the composition comprises 3-5% by weight of the rheology modifier system.

4. The vegan anhydrous semi-solid composition according to claim 3, wherein the particulate includes 10-25% by weight of the composition of a filler.

5. The vegan anhydrous semi-solid composition according to claim 4, wherein the particulate includes 10-25% by weight of the composition of a pigment, a pearlescent agent, or a combination thereof.

6. The vegan anhydrous semi-solid composition according to claim 5, wherein the composition comprises 30-40% by weight of the organic solvent.

7. The vegan anhydrous semi-solid composition according to claim 6, wherein the organic solvent consists of a hydrocarbon-based oil, a glycol, and a carbonate.

8. The vegan anhydrous semi-solid composition according to claim 7, wherein the composition comprises 7.5-12.5% by weight of waxes.

9. The vegan anhydrous semi-solid composition according to claim 1, wherein the vegan anhydrous semi-solid composition is free of surfactants and emulsifiers.

10. The vegan anhydrous semi-solid composition according to claim 9, wherein the vegan anhydrous semi-solid composition consists of:
- the organic solvent;
- the rheology modifier system;
- the waxes;
- the particulate;
- the non-volatile silicone oil; and
- a film former.

11. The vegan anhydrous semi-solid composition according to claim 10, wherein the film former consists of three silicone film formers.

12. A cosmetic product comprising:
- a hand-held container; and
- a vegan anhydrous semi-solid composition according to claim 1.

13. The cosmetic product according to claim 12, wherein the hand-held container is a tube, bottle, or jar.

14. The cosmetic product according to claim 1, wherein the organic solvent consists of a hydrocarbon-based oil, less than 1% by weight of a glycol, and less than 1% by weight of a carbonate.

15. The cosmetic product according to claim 14, wherein the hydrocarbon-based oil is a branched $C_8$-$C_{14}$ alkane.

16. The cosmetic product according to claim 15, wherein the hydrocarbon-based oil is isododecane.

17. The cosmetic product according to claim 16, wherein the isododecane is present in a total amount of 30% to 40% by weight of the composition.

18. The cosmetic product according to claim 1, wherein the composition is free of a volatile silicone oil.

* * * * *